US007824691B2

(12) United States Patent
Balaban

(10) Patent No.: US 7,824,691 B2
(45) Date of Patent: Nov. 2, 2010

(54) **USE OF RIP IN TREATING *STAPHYLOCOCCUS AUREUS* INFECTIONS**

(75) Inventor: Naomi Balaban, Hopkinton, MA (US)

(73) Assignee: Centegen, Inc., Pikesville, MD (US)

( * ) Notice: Subject to any disclaimer, the term of this patent is extended or adjusted under 35 U.S.C. 154(b) by 892 days.

(21) Appl. No.: 11/395,293

(22) Filed: Apr. 3, 2006

(65) Prior Publication Data

US 2007/0071768 A1 Mar. 29, 2007

Related U.S. Application Data

(60) Provisional application No. 60/668,132, filed on Apr. 4, 2005.

(51) Int. Cl.
| | |
|---|---|
| A61K 38/00 | (2006.01) |
| A61K 38/16 | (2006.01) |
| A61K 39/38 | (2006.01) |
| A61K 39/00 | (2006.01) |
| A61K 39/02 | (2006.01) |
| A61K 39/085 | (2006.01) |
| A61K 39/09 | (2006.01) |
| A61K 39/08 | (2006.01) |
| A61K 39/108 | (2006.01) |
| A61K 39/07 | (2006.01) |
| A01N 37/18 | (2006.01) |
| A61F 13/00 | (2006.01) |
| A61F 2/00 | (2006.01) |
| A61F 6/06 | (2006.01) |

(52) U.S. Cl. .............. 424/234.1; 424/184.1; 424/190.1; 424/236.1; 424/237.1; 424/239.1; 424/241.1; 424/243.1; 424/246.1; 424/247.1; 424/257.1; 424/422; 424/423; 424/430; 514/8; 514/2

(58) Field of Classification Search ........................ None
See application file for complete search history.

(56) References Cited

U.S. PATENT DOCUMENTS

| 5,049,322 | A  | * | 9/1991  | Devissaguet et al. ......... 264/4.1 |
|---|---|---|---|---|
| 6,291,431 | B1 | * | 9/2001  | Balaban et al. ............... 514/16 |
| 6,447,786 | B1 |   | 9/2002  | Novick et al. |
| 6,689,878 | B2 | * | 2/2004  | Balaban et al. ............. 536/23.5 |
| 6,706,289 | B2 |   | 3/2004  | Lewis et al. ................. 424/501 |
| 6,747,129 | B1 | * | 6/2004  | Balaban et al. ............. 530/350 |
| 7,067,135 | B2 | * | 6/2006  | Balaban .................... 424/190.1 |
| 7,323,179 | B2 | * | 1/2008  | Balaban .................... 424/234.1 |
| 2002/0102271 | A1 | * | 8/2002 | Balaban et al. .......... 424/190.1 |
| 2003/0050248 | A1 | * | 3/2003 | Wright et al. ................. 514/17 |
| 2004/0072748 | A1 |   | 4/2004 | Balaban |
| 2004/0077534 | A1 | * | 4/2004 | Balaban ....................... 514/12 |
| 2006/0252691 | A1 | * | 11/2006| Balaban ....................... 514/12 |
| 2007/0009566 | A1 | * | 1/2007 | Balaban ..................... 424/423 |
| 2007/0009567 | A1 | * | 1/2007 | Balaban ..................... 424/423 |
| 2007/0009569 | A1 | * | 1/2007 | Balaban ..................... 424/423 |
| 2007/0015685 | A1 | * | 1/2007 | Balaban ....................... 514/2 |
| 2007/0071768 | A1 | * | 3/2007 | Balaban .................... 424/190.1 |
| 2007/0092575 | A1 | * | 4/2007 | Balaban et al. ............. 424/489 |
| 2007/0254006 | A1 | * | 11/2007| Loose et al. ................. 424/423 |
| 2007/0293435 | A1 | * | 12/2007| Balaban et al. ............... 514/18 |
| 2008/0138332 | A1 | * | 6/2008 | Balaban .................... 424/133.1 |
| 2008/0152701 | A1 | * | 6/2008 | Balaban .................... 424/450 |
| 2008/0219976 | A1 | * | 9/2008 | Balaban .................... 424/133.1 |
| 2009/0092578 | A1 | * | 4/2009 | Su et al. ..................... 424/85.2 |

FOREIGN PATENT DOCUMENTS

| EP | 0 395 099 B1 | 10/1990 |
|---|---|---|
| EP | 1 188 831 A2 | 3/2002 |
| WO | 96/10579 | 4/1996 |
| WO | 97/44349 | 11/1997 |
| WO | 99/32133 | 7/1999 |
| WO | 2005/009396 A2 | 2/2005 |
| WO | WO 2006/107944 | * 10/2006 |
| WO | WO 2006/107945 | * 10/2006 |
| WO | WO 2006/107946 | * 10/2006 |
| WO | WO 2006/122127 | * 11/2006 |

OTHER PUBLICATIONS

Ghiselli et al, Shock, 2006, 26/3:296-301.*
Tsang et al, Infection and Immunity, Sep. 2007, 75/9:4528-4533.*
Cirioni et al, J. Infectious Diseases, 2006, 193:180-186.*
Simonetti et al, Antimicrobial Agents and Chemotherapy, Jun. 2008, 52/6:2205-2211.*
Balaban et al, Clinical Orthopaedics and Related Research, 2005, 437:48-54.*
Balaban et al, Antimicrobial Agents and Chemotherapy, Jun. 2007, 51/6:2226-2229.*
Cirioni et al, Antimicrobial Agents and Chemotherapy, Dec. 2007, 51/12:4518-4520.*

(Continued)

Primary Examiner—N. M Minnifield
(74) Attorney, Agent, or Firm—DLA Piper LLP (US)

(57) ABSTRACT

The present composition combines an RNAIII-inhibiting peptide (RIP) with an antimicrobial peptide, such as a cathelicidin, that is capable of binding and neutralizing lipidic and polyanionic components of bacterial cell envelope. In another embodiment, the RIP is combined with an antibiotic, with or without an antimicrobial peptide. The present composition is advantageously used in a method of treatment of bacterial sepsis.

12 Claims, 4 Drawing Sheets

OTHER PUBLICATIONS

March et al, Current Opinion in Biotechnology, 2004, 15:495-502.*
U.S. Appl. No. 11/414,350, filed May 1, 2006, Balaban.
U.S. Appl. No. 11/440,093, filed May 25, 2006, Balaban.
U.S. Appl. No. 11/441,229, filed May 26, 2006, Balaban.
U.S. Appl. No. 11/394,228, filed Mar. 21, 2006, Balaban et al.
U.S. Appl. No. 11/480,825, filed Jul. 6, 2006, Balaban et al.
U.S. Appl. No. 11/395,294, filed Apr. 3, 2006, Balaban.
U.S. Appl. No. 11/430,091, filed May 9, 2006, Balaban et al.
Balaban et al., "Autocrine regulation of toxin synthesis by *Staphylococcus aureus*." *Proc. Nat'l Acad. Sci.* USA 92:1619-1623 (1995).
Balaban et al., "Translation of RNAIII, the *Staphylococcus aureus agr* regulatory RNA molecule, can be activated by a 3'-end deletion." *FEMS Microbiol. Lett.* 133: 155-161 (1995).
Balaban et al., "Autoinducer of virulence as a target for vaccine and therapy against *Staphylococcus aureus*." *Science* 280: 438-440 (1998).
Balaban et al., "Prevention of diseases caused by *Staphylococcus aureus* using the peptide RIP." *Peptides* 21: 1301-1311 (2000).
Balaban et al., "Activation and inhibition of the *Staphylococcus agr* system." *Science* 287: 391a (2000).
Balaban et al., "Regulation of *Staphylococcus aureus* pathogenesis via target of RNAIII-activating Protein (TRAP)." *J. Biol. Chem.* 276: 2658-2667 (2001).
Balaban et al., "Prevention of *Staphylococcus aureus* biofilm on dialysis catheters and adherence to human cells." *Kidney Int'l* 63: 340-345 (2003).
Balaban et al., "Use of the quorum-sensing inhibitor RNAIII-inhibiting peptide to prevent biofilm formation in vivo by drug-resistant *Staphylococcus epidermidis*." *J. Infect. Dis.* 187: 625-630 (2003).
Balaban et al., "A chimeric peptide composed of a dermaseptin derivative and an RNA III-inhibiting peptide prevents graft-associated infections by antibiotic-resistant staphylococci." *Antimicrob. Agents Chemother.* 48: 2544-2550 (2004).
Benincasa et al., "In vitro and in vivo antimicrobial activity of two alpha-helical cathelicidin peptides and of their synthetic analogs." *Peptides* 24:1723-1731 (2003).
Cannon, "Antimicrobial peptides. A family of wound healers." *Nature* 28: 478 (1987).
Cirioni et al., "Prophylactic efficacy of topical temporin A and RNAIII-inhibiting peptide in a subcutaneous rat pouch model of graft infection attributable to staphylococci with intermediate resistance to glycopeptides." *Circulation* 108: 767-771 (2003).
Costerton et al., "Bacterial biofilms: a common cause of persistent infections." *Science* 284: 1318-1322 (1999).
De Kimpe et al., "The cell wall components peptidoglycan and lipoteichoic acid from *Staphylococcus aureus* act in synergy to cause shock and multiple organ failure." *Proc. Nat'l Acad. Sci.* USA 92:10359-10363 (1995).
Dell'Acqua et al., "Suppression of drug-resistant staphylococcal infections by the quorum-sensing inhibitor RNAIII-inhibiting peptide." *J. Infect. Dis.* 190: 318-320 (2004).
Domenico et al., "BisEDT and RIP act in synergy to prevent graft infections by resistant staphylococci." *Peptides* 25: 2047-2053 (2004).
Ganz et al., "Antimicrobial peptides of leukocytes." *Curr. Opin. Hematol.* 4: 53-58 (1997).
Ghiselli et al., "RNAIII-inhibiting peptide and/or nisin inhibit experimental vascular graft infection with methicillin-susceptible and methicillin-resistant *Staphylococcus epidermidis*." *Eur. J. Vasc. Endovasc. Surg.* 27: 603-607 (2004).
Giacometti et al., "RNA III inhibiting peptide inhibits in vivo biofilm formation by drug-resistant *Staphylococcus aureus*." *Antimicrob. Agents Chemother.* 47: 1979-1983 (2003).
Giacometti et al., "RNAIII-inhibiting peptide improves efficacy of clinically used antibiotics in a murine model of staphylococcal sepsis." *Peptides* 26: 169-175 (2005).
Giacometti et al., "Administration of protegrin peptide IB-367 to prevent endotoxin induced mortality in bile duct ligated rats." *Gut* 52: 874-878 (2003).
Giacometti et al., "Cathelicidin peptide sheep myeloid antimicrobial peptide-29 prevents endotoxin-induced mortality in rat models of septic shock." *Am. J. Respir. Crit. Care Med.* 169: 187-194 (2004).
Gough et al., "Antiendotoxin activity of cationic peptide antimicrobial agents." *Infect. Immun.* 64: 4922-4927 (1996).
Gov et al., "RNAIII inhibiting peptide (RIP), a global inhibitor of *Staphylococcus aureus* pathogenesis: structure and function analysis." *Peptides* 22: 1609-1620 (2001).
Gov et al., "Quorum sensing in Staphylococci is regulated via phosphorylation of three conserved histidine residues." *J. Biot. Chem.* 279: 14665-14672 (2004).
Hancock et al., "Cationic peptides: a new source of antibiotics." *Trends Biotechnol.* 6: 82-88 (1998).
Hancock et al., "The role of antimicrobial peptides in animal defenses." *Proc. Nat'l Acad. Sci.* USA 97: 8856-8861 (2000).
Hancock, "Cationic peptides: effectors in innate immunity and novel antimicrobials." *Lancet Infect. Dis.* 1: 156-164 (2001).
Hancock, "Host defence (cationic) peptides: what is their future clinical potential?" *Drugs.* 57: 469-473 (19999).
Hartman et al., "Quorum sensing: potential means of treating gram-negative infections?" *Lancet* 351: 848-849 (1998).
Hwang et al., "Structure-function relationships of antimicrobial peptides." *Biochem. Cell. Biol.* 76: 235-246 (1998).
Ji et al., "Cell density control of Staphylococcus virulence mediated by an octapeptide pheromone." *Proc. Nat'l Acad. Sci.* USA 92: 12055-12059 (1995).
Ji et al., "Bacterial interference caused by autoinducing peptide variants." *Science* 276: 2027-2030 (1997).
Korem et al., "Characterization of RAP, a quorum sensing activator of *Staphylococcus aureus*." *FEMS Microbiol. Lett.* 223: 167-175 (2003).
Korem et al., "Transcriptional profiling of target of RNAIII-activating protein, a master regulator of staphylococcal virulence." *Infect. Immun.* 73: 6220-6228 (2005).
Lee, "An experimental vaccine that targets staphylococcal virulence." *Trends Micrbiol.* 6: 461-463 (1998).
Mayville et al., "Structure-activity analysis of synthetic autoinducing thiolactone peptides from *Staphylococcus aureus* responsible for virulence." *Proc. Nat'l Acad. Sci.* USA 96: 1218-1223 (1999).
Morfeldt et al., "Activation of alpha-toxin translation in *Staphylococcus aureus* by the *trans*-encoded antisense RNA, RNAIII." *Embo J.* 14(18): 4569-4577 (1995).
Novick et al., "Synthesis of staphylococcal virulence factors is controlled by a regulatory RNA molecule." *EMBO J.* 12(120): 3967-3975 (1993).
Novick et al., "Virulence gene regulation by peptides in staphylococci and other Gram-positive bacteria." *Curr. Opin. Microbiol.* 2: 40-45 (1999).
Otto, "Quorum-sensing control in Staphylococci—a target for antimicrobial drug therapy?" *FEMS Microbiol. Lett.* 241: 135-141 (2004).
Panlilio et al., "Methicillin-resistant *Staphylococcus aureus* in U.S. hospitals, 1975-1991." *Infect. Control Hosp. Epidemiol.* 13: 582-586 (1992).
Ribeiro et al., "Treatment efficacy of the lead RNAIII-inhibiting peptide YSPWTNF-NH$_2$ in acquired *Staphylococcus aureus* sepsis: a histopathological assessment." *Peptides* 24: 1829-1836 (2003).
Scott et al., "Biological properties of structurally related alpha-helical cationic antimicrobial peptides," *Infect. Immun.* 67: 2005-2009 (1999).
Scott et al., "Interaction of cationic peptides with lipoteichoic acid and gram-positive bacteria." *Infect. Immun.* 67: 6445-6453 (1999).
Silverstein et al., "Host defense against bacterial and fungal infections." Microbiology, B.D. Davis, et al., eds., 4th ed., J.B. Lippincott Co., Philadelphia, PA, Chapter 21, pp. 485-505 (1980).
Skerlavaj et al., "Biological characterization of two novel cathelicidin-derived peptides and identification of structural requirements for their antimicrobial and cell lytic activities." *J. Biol. Chem.* 271: 28375-28381 (1996).
Smith et al., "Induction and inhibition of *Pseudomonas aeruginosa* quorum sensing by synthetic autoinducer analogs." *Chem. Biol.* 10: 81-89 (2003).

Stark et al., "Cationic hydrophobic peptides with antimicrobial activity." *Antimicrob. Agents Chemother*. 46: 3585-3590 (2002).

Strauss, "A possible new approach to combating Staph infections." *Science* 280: 379 (1998).

University of Nebraska Medical Center, "Welcome to the antimicrobial peptide database," at http://aps.unmc.edu/AP/main.php (last accessed Feb. 24, 2006).

Vieira-Da-Motta et al., "RNAIII inhibiting peptide (RIP) inhibits *agr*-regulated toxin production." *Peptides* 22: 1621-1627 (2001).

Vieira-Da-Motta et al., "Repression of enterotoxin production in *Staphylococcus aureus* by quorum sensing effectors." 41st Interscience Conference on Antimicrobial Agents and Chemotherapy, Abstract B-955, p. 46 (Sep. 22-25, 2001).

Yang et al., "Inhibition of *Staphylococcus aureus* pathogenesis in vitro and in vivo by RAP-binding peptides." *Peptides* 24: 1823-1828 (2003).

Yang et al., "A novel peptide screened by phage display can mimic TRAP antigen epitope against *Staphylococcus aureus* infections." *J. Biol. Chem*. 280: 27431-27435 (2005).

Yang et al., "A novel peptide isolated from phage library to substitute a complex system for a vaccine against staphylococci infection." *Vaccine* 24: 1117-1123 (2006).

Zanetti et al., "Cathelicidin peptides as candidates for a novel class of antimicrobials." *Curr. Pharm. Des*. 8: 779-793 (2002).

Zanetti, "Cathelicidins, multifunctional peptides of the innate immunity." *J. Leukoc. Biol*. 75: 39-48 (2004).

Zanetti et al., "Cathelicidins: a novel protein family with a common proregion and a variable C-terminal antimicrobial domain." *FEBS Lett*. 374: 1-5 (1995).

* cited by examiner

USE OF RIP IN TREATING STAPHYLOCOCCUS AUREUS INFECTIONS

CROSS REFERENCE TO RELATED CASES

This application claims the benefit of Provisional U.S. Application Ser. No. 60/668,132, filed Apr. 4, 2005, which is incorporated by reference herein in its entirety.

BACKGROUND

1. Technical Field

This application relates generally to pharmacological compositions and methods for treating or reducing the risk of bacterial infection and, in particular, to compositions comprising an RNAIII-inhibiting peptide and an antimicrobial peptide and/or an antibiotic that is an aminoglycoside, beta-lactam, caphalosoprin or vancomycin.

2. Background of the Technology

Sepsis

Sepsis remains a leading cause of death, despite improvements in antimicrobial drugs and better supportive care. Sepsis is associated with systemic inflammation, circulatory failure, and multiple organ dysfunction syndrome (MODS). Both Gram-positive microbes, such as *Staphylococcus aureus*, and Gram-negative bacteria can cause sepsis. The incidence of sepsis is currently on the rise. Angus et al., *Crit. Care Med.* 29: 1303-10 (2001). Gram-negative bacteria release lipopolysaccharide (LPS), or endotoxin, from their outer membrane, which elicits septic shock. By contrast, some Gram-positive bacteria cause septic shock by the release of enterotoxins, 23 to 29 kDa polypeptides in the bacterial superantigen protein family, such as toxic shock syndrome toxin-1 (TSST-1), and exotoxins, such as pyrogenic exotoxin A. Exotoxins are soluble substances that alter the normal metabolism of host cells with deleterious effects on the host, while enterotoxins are exotoxins that are specific for intestinal cells. See De Kimpe et al., *Proc. Nat'l Acad. Sci. USA* 92: 10359-63 (1995); Kengatharan et al., *J. Exp. Med.* 188: 305-15 (1998); Llewelyn et al., *Lancet Infect. Dis.* 2: 56-162 (2002); Van Amersfoort et al., *Clin. Microbiol. Rev.* 16: 379-414 (2003).

Gram-positive bacteria cell wall components peptidoglygan (PG) and lipoteichoic acid (LTA) also have been shown to produce an inflammatory response. PG has a rigid structure and consists of repeating units of N-acetylglucosamine (β1-4)-linked to N-acetylmuramic acid. LTA molecules comprise repeating poly-(polyolphosphate) units and are highly variable for the presence of alditol groups that are modified with glycosil residues or D-alanine. LTA activates macrophages and polymorphonuclear leukocytes by binding to CD14, a surface receptor that also mediates responses to lipopolysaccharides. LTA acts synergistically with PG to release TNF-α and IL-6 and induce nitric oxide synthase (NOS) among other things, leading to circulatory failure, MODS and death. See De Kimpe (1995); Kengatharan (1998); Heumann et al., *Infect. Immunol.* 62: 2715-21 (1994); Scott et al., *Infect. Immunol.* 69: 875-88 (2001).

Quorum Sensing and RNAIII—Inhibiting Peptide

Recent studies have evidenced the importance of quorum-sensing in the pathology of bacterial species including *Vibrio cholerae, Pseudomonas aeruginosa*, and *Staphylococcus aureus*. Quorum-sensing is a mechanism through which a bacterial population receives input from neighboring cells and elicits an appropriate response to enable itself to survive within the host. See Balaban et al., *Science* 280: 438-40 (1998); Miller et al., *Cell* 110: 303-14 (2002); Hentzer et al., *EMBO J.* 22: 3803-15 (2003); Korem et al., *FEMS Microbiol. Lett.* 223: 167-75 (2003). In *Staphylococcus*, quorum-sensing controls the expression of proteins implicated in bacterial virulence, including colonization, dissemination, and production of multiple toxins involved in disease promotion. Some of these virulence factors are enterotoxins and toxic-shock syndrome toxin-1 (TSST-1), which act as superantigens to cause over-stimulation of the host immune system, causing excessive release of cytokines and inducing the hyper-proliferation of T cells.

In a quorum-sensing system in *S. aureus*, the effector quorum-sensing molecule RNAIII-activating peptide (RAP) phosphorylates "target of RNAIII-activating protein" (TRAP), a 21 kDa protein that is highly conserved among staphylococci. TRAP phosphorylation promotes bacterial adhesion and the downstream production of a regulatory RNA molecule termed RNAIII, which is responsible for toxin synthesis. Balaban (1998); Balaban et al., *J. Biol. Chem.* 276: 2658-67 (2001). An antagonist of RAP called RNAIII-inhibiting peptide (RIP) inhibits the phosphorylation of TRAP and thereby strongly inhibits the downstream production of virulence factors, bacterial adhesion, biofilm formation, and infections in vivo. The mechanism of action of RIP is different from common antibiotics: instead of killing bacteria, RIP inhibits bacterial cell-cell communication, rendering the bacteria more vulnerable to host defense mechanisms. See Balaban (1998); Balaban et al., *Peptides* 21: 1301-11 (2000); Gov et al., *Peptides* 22: 1609-20 (2001); Balaban et al., *J. Infect. Dis.* 187:625-30 (2003); Cirioni et al., *Circulation* 108: 767-71 (2003); Ribeiro et al., *Peptides* 24: 1829-36 (2003); Giacometti et al., *Antimicrob. Agents Chemother.* 47: 1979-83 (2003); Balaban et al., *Kidney Int.* 23: 340-45 (2003); Balaban et al., *Antimicrob. Agents Chemother.* 48: 2544-50 (2004); Dell'Acqua et al., *J. Infect. Dis.* 190: 318-20 (2004).

Antimicrobial Peptides

Genetically encoded antimicrobial peptides are an important component of the innate immune response in most multicellular organisms that represents a first line of host defense against an array of microorganisms. Antimicrobial peptides have pleiotropic immunomodulatory functions and are endowed with direct antimicrobial activity and LTA/LPS-binding capacity. Antimicrobial peptides in circulating phagocytes contribute to the killing of engulfed microorganisms, and they act as a local defense mechanism in epithelial surfaces, protecting anatomical compartments from microbial invasion. See Cannon, *Nature* 328:478 (1987); Scott (1999); Hancock et al., *Proc. Nat'l Acad. Sci. USA* 97: 856-61 (2000); Giacometti et al., *Gut* 52: 874-78 (2003); Gough et al., *Infect. Immun.* 64:4922-27 (1996).

Cathelicidins are a family of related antimicrobial peptides that are produced as inactive precursors by several mammalian species on epithelial surfaces and within the granules of phagocytic cells. Cathelicidins exert a broad spectrum of antimicrobial activity against Gram-negative bacteria, Gram-positive bacteria and fungi with a wide overlap in specificity but also with significant differences in potency among antimicrobial peptide species. Like other antimicrobial peptides, cathelicidins bind LPS and neutralize its pro-inflammatory effects. See Zanetti et al., *FEBS Lett.* 374: 1-5 (1995); Zanetti et al., *Curr. Pharm. Des.* 8: 779-93 (2002); Zanetti et al., *J. Leuk. Biol.* 75: 39-48 (2004); Giacometti et al., *Amer. J. Resp. Crit. Care Med.* 169: 187-94 (2004).

Cathelicidins include BMAP-28, a peptide 27 amino acids in length with a primary amino sequence of GGL-RSLGRKILRAWKKYGPIIVPIIRI-NH$_2$ (SEQ ID NO: 1)

and an amidated C-terminus. BAMP-28 kills antibiotic-resistant clinical isolates in vitro at submicromolar concentrations, and it retains a strong and broad activity spectrum in physiologic salt concentrations. BMAP-28 efficiently protects mice in vivo from lethal intraperitoneal infections in an acute peritonitis model. See Skerlavaj et al., *J. Biol. Chem.* 71: 28375-81 (1996); Benincasa et al., *Peptides* 24: 1723-31 (2003).

Conventional antibiotics are becoming less effective in dealing with the pathologies underlying sepsis and other serious diseases. For example, staphylococci currently are regarded as "super bugs" because of their capacity to acquire antibiotic resistance. Accordingly, there is an ongoing need for better compositions and methods to treat bacterial infections, particularly from Gram-positive bacteria such as *Staphylococcus aureus*.

SUMMARY

The present invention provides a therapeutic composition comprising a RIP and an antimicrobial peptide to meet the ongoing need for treating diseases associated with bacterial infection, particularly staphylococcal sepsis. RIP by itself inhibits LTA-induced production of TNF-α and NO, and RIP and a cathelicidin antimicrobial peptide synergistically inhibit LTA-induced production of TNF-α and NO. When administered in vivo, RIP by itself reduces mortality and bacteremia, and RIP and a cathelicidin antimicrobial peptides act synergistically in vivo to reduce mortality and bacteremia. While the present composition can be used in combination with conventional antibiotic chemotherapy, the present composition advantageously is effective against antibiotic resistant bacteria and may be used as an alternative to convention chemotherapy.

According to a first aspect of the invention, a composition comprises a RIP and a polycationic antimicrobial peptide that is capable of binding and neutralizing a lipidic and polyanionic component of a bacterial cell envelope, such as LTA or LPS. Antimicrobial peptides that are useful in the present composition include a cathelicidin, such as a human cathelicidin, or BMAP-28.

The composition further may comprise conventional antibiotics or other pharmaceutically acceptable agents, such as agents that assist or delay adsorption of the composition by the host. Pharmaceutical agents, e.g., liposomes or nanoparticles, may be included to assist in delivering or targeting the composition to a desired location or cell type. The composition may be formulated for administration by any acceptable method, such as topical application, ingestion, or parenteral administration or as a coating on a medical device.

The RIP may comprise five contiguous amino acids of the sequence YX$_2$PX$_1$TNF (SEQ ID NO: 2), where X$_1$ is C, W, I or a modified amino acid, and X$_2$ is K or S; or amino acids having a sequence that differs from the sequence YX$_2$PX$_1$TNF (SEQ ID NO: 2) by two substitutions or deletions, where X$_1$ is C, W, I or a modified amino acid, and X$_2$ is K or S. In one embodiment, the RIP does not consist of the sequence YSPX$_1$TNF (SEQ ID NO: 3), where X$_1$ is C, W, I or a modified amino acid. Alternatively, the RIP may comprise amino acids having a sequence that differs from the sequence YX$_2$PX$_1$TNF (SEQ ID NO: 2) by one substitution or deletion, where X$_1$ is C, W, I or a modified amino acid, and X$_2$ is K or S. In various other embodiments, the RIP comprises the amino acid sequences YKPX$_1$TNF (SEQ ID NO: 4), where X$_1$ is C, W, I or a modified amino acid; the amino acid sequence IKKYX$_2$PX$_1$TNF (SEQ ID NO: 1), where X$_1$ is C, W, I or a modified amino acid and X$_2$ is K or S; or one of the sequences PCTNF (SEQ ID NO: 6), YKPITNF (SEQ ID NO: 7), or YKPWTNF (SEQ ID NO: 8). The RIP may be ten amino acids in length and may comprise about 0.1% to 50% by weight of the composition, or about 2% to 20% by weight of the composition.

According to a second aspect of the invention, a method of treating a disease associated with a bacterial infection comprises administering a composition comprising a RIP and an antimicrobial peptide that is capable of binding and neutralizing a lipidic and polyanionic component of a bacterial cell envelope, such as LTA or LPS, to a mammalian individual. The method of the invention is particularly advantageous in treating or reducing the risk of a bacterial infection that comprises an inflammatory response caused by a lipidic and polyanionic component of a bacterial cell envelope, such as bacterial sepsis. The method may be used to treat a systemic bacterial infection, or an infection localized to particular tissue, skin or region of the body. The infection also may be associated with other diseases, such as cellulitis, keratitis, osteomyelitis, septic arthritis or mastitis. The administering may be by a topical, oral, intravenous, intraperitoneal, intramuscular, transdermal, nasally, or iontophoretic route, such as by a depot-style system, an encapsulated form, or an implant.

The present method also is useful in the treatment of bacterial infection associated with biofilms, or in reducing the risk of a disease associated with biofilms, particularly those whose pathologies involve an inflammatory response caused by a lipidic and polyanionic component of a bacterial cell envelope. For example, the present composition may be used to coat devices inserted into an individual to reduce the risk that the implanted device will develop a biofilm.

The method further may be practiced on an individual at risk of having or suspected of having an infection caused by bacteria, such as an individual who is suffering from burns, trauma, etc. Alternatively, the composition may be administered to treat an ongoing infection, delay the onset of symptoms of bacterial infection, or reduce the risk of developing an infection.

In one embodiment, the individual receiving the composition is infected or at risk of infection by Gram-positive bacteria, such as *Streptococcus* ssp, including *S. aureus* and *S. epidermidis*, or an antibiotic resistant strain thereof. In other embodiments, the pathogen may be *Listeria* spp, including *L. innocua*, and *L. monoctogenes, Lactococcus* spp, *Enterococcus* spp, *Escherichia coli, Clostridium acetobtylicum*, and *Bacillus* spp, including *B. subtilus, B. anthracis*, and *B. cereus* or an antibiotic resistant strain thereof. The method may comprise administering the composition by any pharmacologically acceptable means, such as topical application, ingestion, parenteral administration, or as a coating on a medical device.

According to a third aspect of the invention, a method of treating a disease associated with a bacterial infection comprises administering a composition comprising a RIP and an antibiotic that is an aminoglycoside, beta-lactam, caphalosoprin or vancomycin in an amount effective to treat or reduce the risk of bacterial infection in a mammalian individual, e.g., a human, receiving the composition. In particular, the antibiotic may be imipenem or vancomycin. The composition may further comprise an antimicrobial peptide. In a fourth aspect of the invention, a method of treating or reducing the risk of bacterial infection in a mammalian individual, e.g., a human, comprises administering this same composition to the individual.

DETAILED DESCRIPTION

Figure 1:
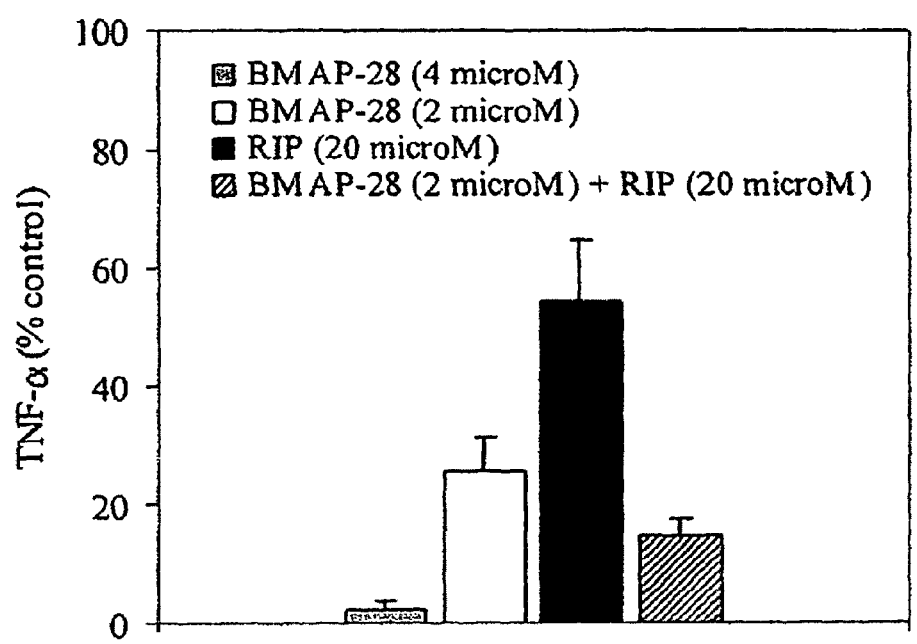
FIG. 1 depicts the effect of RIP and the bovine antimicrobial peptide BMAP-28 on LTA-stimulated TNF-α production as a percentage of control levels in cultured RAW264.7 cells. TNF-α levels in the culture supernatant were measured 24 h after LTA stimulation in the presence of the reagents shown in the figure key.

The present composition combines an RNAIII-inhibiting peptide with a polycationic antimicrobial peptide that is capable of binding and neutralizing a lipidic and polyanionic component of a bacterial cell envelope, such as LTA or LPS. The antimicrobial peptide may be a cathelicidin. RNAIII-inhibiting peptides of the invention generally are those that are able to inhibit RNAIII activity, decrease the phosphorylation TRAP, inhibit production of cytokines or NO in an in vitro model, or display related activities. Recognizing the importance of cell wall components and exotoxin production in the pathology of bacterial sepsis, the present composition is advantageously used in a method of treatment of bacterial sepsis or a similar condition in which bacterial pathology is related to a lipidic and polyanionic component of a bacterial cell envelope, such as LTA or LPS.

The present composition alternatively or additionally combines a RIP with a conventional antibiotic, such as a beta-lactam, an aminoglycoside, cephalosporin or vancomycin. Such a composition is particularly advantageously when the infected individual is infected with, or is at risk of being infected with, antibiotic resistant bacteria, since RIP exerts its antibacterial effects by a mechanism separate from such conventional antibiotics. For example, such a composition may be particularly useful for treating or reducing the risk of infections associated with biofilms, which tend to be recalcitrant to chemotherapy with conventional antibiotics. This recalcitrance necessitates the prolonged use of antibiotics in the affected individual, which promotes the rise of resistant bacteria. Resistance to some antibiotics, e.g., antibiotics of the penicillin family and more recently vancomyicn, has become so widespread that the use of these antibiotics is severely restricted. It is perceived that use of the present compositions comprising RIP will revive the use of these antibiotics, however, because of the ability of RIP to eliminate or reduce biofilms, thereby reducing an obstacle to prolonged antibiotic therapy and overcoming some of the resistance developed to these antibiotics.

In one embodiment, the method may be used to treat or reduce the risk of infection by Gram-positive bacteria. The method of the invention also is useful to treat diseases like cellulitis, keratitis, osteomyelitis, septic arthritis or mastitis. The present composition may be administered in an amount effective to treat an infection by *Staphylococcus* in a host individual, but the composition also is useful in treating infections caused by *Listeria* spp, including *L. innocua*, and *L. monoclogenes, Lactococcus* spp, *Enterococcus* spp, *Escherichia coli, Clostridium acetobtylicum*, and *Bacillus* spp., including *B. subtilus, B. anthracis*, and *B. cereus* or an antibiotic resistant strain thereof.

RNAIII-Inhibiting Peptides of the Invention

The quorum-sensing inhibitor RIP does not affect bacterial growth but reduces the pathogenic potential of the bacteria by interfering with the signal transduction that leads to production of exotoxins. RIP blocks toxin production by inhibiting the phosphorylation of its target molecule TRAP, which is an upstream activator of the agr locus. By contrast, the mechanism of action of antimicrobial peptides comprises disrupting the bacterial outer membrane barrier and perturbing the cytoplasmic membrane. In addition, polycationic antimicrobial peptides bind and neutralize lipidic and polyanionic components of the bacterial cell envelope, like LPS and LTA. Because RIP and antimicrobial peptides act by different mechanisms, the two can act synergistically to treat bacterial infections.

RIP comprises the general formula $YX_2PX_1TNF$ (SEQ ID NO: 2), where $X_1$ is C, W, I or a modified amino acid and $X_2$ is K or S. Specific RIP sequences are disclosed in U.S. Pat. No. 6,291,431 and Gov et al., *Peptides* 22:1609-20 (2001), incorporated herein by reference. RIP sequences include polypeptides comprising the amino acid sequence $KKYX_2PX_1TN$ (SEQ ID NO: 9), where $X_1$ is C, W, I or a modified amino acid and $X_2$ is K or S. RIP sequences also include polypeptides comprising $YSPX_1TNF$ (SEQ ID NO: 10), where $X_1$ is C or W, and YKPITN (SEQ ID NO: 11). In one embodiment, the RIP comprising the general formula $YX_2PX_1TNF$ (SEQ ID NO: 2) above is further modified by one or two amino acid substitutions, deletions, and other modifications, provided the RIP exhibits activity.

Assay Systems for Determining Activity of RIP and RIP Formulations

The mechanism through which RIP inhibits quorum-sensing mechanisms, as discussed above, involves inhibition of the phosphorylation of TRAP. There is evidence of the presence of TRAP and TRAP phosphorylation in *S. epidermidis*, indicating that there is a similar quorum sensing mechanisms both in *S. aureus* and in *S. epidermidis* and the potential for RIP to interfere with biofilm formation and infections caused by both species. In addition, there is evidence that TRAP is conserved among all staphylococcal strains and species; therefore, RIP should be effective against any type of *Staphylococcus*. Further, other infection-causing bacteria appear to have proteins with sequence similarity to TRAP, including *Bacillus subtilus, Bacillus anthracis, Bacillus cereus, Listeria innocua,* and *Listeria monoctogenes*. Moreover, RAP is an ortholog of the ribosomal protein L2, encoded by the rplB gene. See Korem et al., *FEMS Microbiol. Lett.* 223: 167-75 (2003), which is incorporated by reference herein with regard to its description of RAP orthologs encoded by the rplB gene.

L2 is highly conserved among bacteria, including *Streptococcus* ssp, *Listeria* spp, *Lactococcus* spp, *Enterococcus* spp, *Escherichia coli, Clostridium acetobtylicum*, and *Bacillus* spp. This finding indicates that treatment aimed at disturbing the function of RAP in *S. aureus* also will be effective in treating L2-synthesizing bacteria as well.

RNAIII-inhibiting peptides according to the invention exhibit activity, which can be assayed using a number of routine screens. For example, RIPs are capable of inhibiting production of RNAIII or TRAP phosphorylation in vitro using the assay methods described in Balaban et al., *Peptides* 21:1301-11 (2000), incorporated herein by reference. RIP activity includes inhibiting *staphylococcal* infections. RIP inhibits *Staphylococci* from adhering and from producing toxins by interfering with the known function of a *staphylococcal* quorum-sensing system. RIP competes with RAP induction of TRAP phosphorylation, thus leading to inhibition of the phosphorylation of TRAP. See Balaban et al., *J Biol. Chem.* 276: 2658-67 (2001). This leads to a decrease in cell adhesion and biofilm formation, to inhibition of RNAIII synthesis and to suppression of the virulence phenotype. See Balaban et al., *Science* 280: 438-40 (1998). The amide form of a synthetic RIP analogue YSPWTNF(-NH$_2$) (SEQ ID NO: 12) effectively inhibits RNAIII in vitro and suppresses *S. aureus* infections in vivo, including cellulitis (tested in mice against *S. aureus* Smith Diffuse), septic arthritis (tested in mice against *S. aureus* LS-1), keratitis (tested in rabbits against *S. aureus* 8325-4), osteomyelitis (tested in rabbits against *S. aureus* MS), and mastitis (tested in cows against *S. aureus* Newbould 305, AE-1, and environmental infections). See Balaban et al., *Peptides* 21:1301-11 (2000) and Table 1. These findings demonstrate the range of RIP activities and screens available to assay for RIP activity and further indicate that RIP can serve as a useful therapeutic molecule to prevent and suppress *staphylococcal* infections.

assay can detect rnaiii or virulence factor transcription using hybridization techniques that also are well known in the art.

In Vitro High Throughput Analysis of RIP Formulations

The following screening assay for RIP compositions exemplifies the types of assays that may be used to determine whether a particular RIP or RIP composition or formulation exhibits the desired level of biological activity. In this assay system, agr expression is tested in a high throughput assay using an RNAIII reporter gene assay, which is confirmed by Northern blotting. *S. aureus* cells in early exponential growth ($2 \times 10^7$ colony forming units (CFU)) containing the rnaiii:: blaZ fusion construct are grown with increasing concentrations of the test RIP formulations in 96 well plates at 37° C. with shaking for 2.5-5 hrs. In this assay, β-lactamase acts as a reporter gene for RNAIII. Bacterial viability is tested by determining OD 650 nm and further by plating to determine CFU. β-lactamase activity is measured by adding nitrocefin, a substrate for β-lactamase. Hydrolysis of nitrocefin by β-lactamase is indicated by a change in relative adsorption at 490 nm and 650 nm, where yellow color indicates no RNAIII synthesis, and pink color indicates RNAIII synthesis.

Formulations showing efficacy in the high throughput assay are further confirmed by Northern blotting. Bacteria are similarly grown with candidate RIP formulations. Cells are then collected by centrifugation, and total RNA is extracted and separated by agarose gel electrophoresis and Northern blotted. RNAIII is detected by hybridization to radiolabeled RNAIII-specific DNA produced by PCR, for example. Control formulations, containing, for example, random peptides, are tested at 0-10 μg/$10^7$ bacteria.

In Vivo Analysis of RIP Formulations

Candidate peptides also can be assayed for activity in vivo, for example by screening for an effect on *Staphylococcus* virulence factor production in a non-human animal model. The candidate agent is administered to an animal that has

TABLE 1

| Infection | Model | S. aureus strain | Animals tested (n) −RIP | Animals tested (n) +RIP | % animals disease free | P |
|---|---|---|---|---|---|---|
| Osteomyelitis | Rabbit | MS | 7 | 8 | 58 | 0.02 |
| Sepsis | Mouse | LS-1 | 10 | 11 | 44 | 0.04 |
| Arthritus | Mouse | LS-1 | 10 | 10 | 60 | 0.006 |
| Keratitis | Rabbit | 8325-4 | 8 | 8 | 40 | 0.015 |
| Mastitis | Cow | Newbould/AE-1 | 6 | 7 | 70–100 | <0.05 |
| Cellulitis/sepsis | Mouse | Smith diffuse | 22 | 20 | Up to 100 | 0.02 |
| Graft injection | Rat | MRSA, MRSE, VISA, VISE, GISA, GISE, MSSA, MSSE | >1000 | >1000 | Up to 100 | <0.05 |

The screening assay can be a binding assay, wherein one or more of the molecules may be joined to a label that provides a detectable signal. Purified RIP may be used to determine a three-dimensional crystal structure, which can be used for modeling intermolecular interactions. Alternatively, the screening assay can determine the effect of a candidate RIP on RNAIII production and/or virulence factor production. For example, the effect of the candidate peptide on rnaiii transcription in *Staphylococcus* can be measured. Such screening assays can utilize recombinant host cells containing reporter gene systems such as CAT (chloramphenicol acetyltransferase), β-galactosidase, and the like, according to well-known procedures in the art. Alternatively, the screening been infected with *Staphylococcus* or that has received an infectious dose of *Staphylococcus* in conjunction with the candidate agent. The candidate agent can be administered in any manner appropriate for a desired result. For example, the candidate agent can be administered by injection intravenously, intramuscularly, subcutaneously, or directly into the tissue in which the desired affect is to be achieved, or the candidate can be delivered topically, orally, etc. The agent can be used to coat a device that will then be implanted into the animal. The effect of agent can be monitored by any suitable method, such as assessing the number and size of *Staphylococcus*-associated lesions, microbiological evidence of infection, overall health, etc.

The selected animal model will vary with a number of factors known in the art, including the particular pathogenic strain of *Staphylococcus* or targeted disease against which candidate agents are to be screened. For example, when assessing the ability of the RIP formulation to suppress infections associated with toxin production, a mouse sepsis/cellulitis model is particularly useful. Balaban et al., *Science* 280: 438-40 (1998). This model is particularly preferred when, for example, the formulation comprises a RIP and a polycationic antimicrobial peptide that is capable of binding and neutralizing bacterial exotoxins and toxic cell wall components, which otherwise may induce an inflammatory response and toxic shock syndrome.

In the mouse sepsis cellulitis model, hairless immunocompetent mice (n=10) typically are challenged by a subcutaneous injection with 100 μL saline containing $5 \times 10^8$ CFU *S. aureus* strain Smith diffuse together with cytodex beads. Formulated RIP is administered by intravenous administration or orally by gavage at 10 times the i.v. dose. A typical i.v. dose will be <10 mg RIP/kg host body weight. Animals are observed for the five days and lesions are measured. It is expected that some of the animals will die of sepsis within the first 48 hrs due to the infection and others will develop lesions of various sizes.

A rat graft model is especially useful because it can be used to assess the ability of a formulation to suppress infections associated with biofilm formation. Giacometti et al., *Antimicrob. Agents Chemother.* 47: 1979-83 (2003); Cirioni et al., *Circulation* 108: 767-71 (2003); Balaban et al., *J. Infect. Dis.* 187: 625-30 (2003). This model is highly relevant to the clinical setting because it provides a time interval between bacterial challenge and biofilm infection, typically within 72 hours, allowing testing of the optimal route of administration and dose of the RIP formulation. This model provides a more challenging test of activity because biofilms are known to be extremely resistant to antibiotics.

Using the rat graft model, RIP was shown to reduce infection by four orders of magnitude when grafts were soaked with 20 μg/mL RIP for 20 minutes or when RIP was injected by an intraperitoneal route at 10 mg RIP/kg body weight. These results with the rat graft model will be repeated with the most promising RIP formulations as determined by the in vitro assays described above, using higher or lower RIP concentrations than used with RIP alone. That is, formulation efficacy can be compared to intraperitoneal RIP administration at doses known to be effective. Administering RIP locally and parenterally at the time of surgery is 100% effective in preventing infection in this model system. Dell'Acqua et al., *J. Infect. Dis.* 190: 318-20 (2004). RIP formulations of the invention thus preferably can be carried out under the same or similar conditions. RIP formulation can be administered daily before and/or after biofilm formation for 0-6 days after bacterial challenge.

In a typical experiment, Wistar adult male rats (n=10) are anesthetized, and a subcutaneous pocket is made on each side of the median line by a 1.5 cm incision. 1-cm$^2$ sterile collagen-sealed double velour knitted polyethylene terephthalate (Dacron) grafts ALBOGRAFT™, Italy) are soaked with saline, RIP, or a RIP formulation and implanted into the pockets. Pockets are closed with skin clips, and $2 \times 10^7$ CFU/mL bacteria are inoculated onto the graft surface using a tuberculin syringe to create a subcutaneous fluid-filled pocket. The animals are returned to individual cages and examined daily. Animals receive an intravenous or oral administration of RIP or a RIP formulation 0-6 days after the graft infection. Free RIP is administered via an intraperitoneal route as a positive control. Grafts are explanted at 7 days following implantation and CFU are according to known procedures, e.g., Giacometti et al. (2003). The explanted grafts are placed in sterile tubes, washed in sterile saline solution, placed in tubes containing 10 mL of phosphate-buffered saline solution, and sonicated for 5 minutes to remove the adherent bacteria from the grafts. After sonication, grafts are microscopically checked to verify that all bacteria are removed. Quantification of viable bacteria is performed by culturing serial dilutions (0.1 mL) of the bacterial suspension on blood agar plates. All plates are incubated at 37° C. for 48 hours and evaluated for number of CFUs per plate. Of note is that no significant differences in cell viability (CFU/mL) were present upon testing the effect of sonication for up to 10 minutes on either antibiotic sensitive or antibiotic resistant bacteria. The limit of detection for this method is approximately 10 CFU/mL.

Antimicrobial Peptides of the Invention

Antimicrobial peptides useful for the present invention have the ability to bind and neutralize lipidic and polyanionic components of the bacterial cell envelope, like LPS and LTA. The lipidic and polyanionic component may be embedded in the bacterial cell envelop or in soluble form. The antimicrobial peptide in either case binds the component and prevents or inhibits its ability to provoke an inflammatory response in the host. For Gram-negative organisms, cationic antimicrobial peptides may bind LPS, thereby detoxifying its endotoxic activity. See Scott et al., *Infect. Immun.* 67: 2005-09 (1999). Similarly, for Gram-positive bacteria, cationic antimicrobial peptides may bind and neutralize LTA. See Scott (2001). In one embodiment of the invention, the antimicrobial peptide binds LTA or teichoic acid of Gram-positive bacteria.

Antimicrobial peptides have a broad spectrum of activities, killing or neutralizing both gram-negative and gram-positive bacteria, including antibiotic-resistant strains. See Hancock, *Lancet Infect. Dis.* 1: 156-64 (2001). Wang, University of Nebraska Medical Center, Antimicrobial Peptide Database, at aps.unmc.edu/AP/main.php (last modified Mar. 5, 2005), which is incorporated herein by reference in its entirety, provides a database of about 500 antimicrobial peptides with antibacterial activity that potentially are useful for the present invention. Antimicrobial peptides usually are made up of between 12 and 50 amino acid residues and are polycationic. Usually about 50% of their amino acids are hydrophobic, and they are generally amphipathic, where their primary amino acid sequence comprises alternating hydrophobic and polar residues. Antimicrobial peptides fit into one of four structural categories: (i) .beta.-sheet structures that are stabilized by multiple disulfide bonds (e.g., human defensin-1), (ii) covalently stabilized loop structures (e.g., bactenecin), (iii) tryptophan (Trp)-rich, extended helical peptides (e.g., indolicidin), and (iv) amphipathic .alpha.-helices (e.g., the magainins and cecropins). See Hwang et al., *Biochem. Cell Biol.* 76: 235-46 (1998); Stark et al., *Antimicrob. Agents Chemother* 46: 3585-90 (2002).

The cathelicidins, a recently described class of antimicrobial peptides occurring at least in humans, cows, sheep, rabbits, mice, and pigs, utilize all of these structural motifs. See Ganz et al., *Curr. Opinion Hematol.* 4: 53-58 (1997). The cathelicidins share a highly conserved N-terminal propeptide segment of approximately 100 amino acids and a C-terminal domain that encodes the antimicrobial peptide motif. See Hwang et al., *Biochem. Cell Biol.* 76: 235-46 (1998). In humans, neutrophil activation leads to elastase-mediated endoproteolytic cleavage and generation of the C-terminal antimicrobial peptide. The human cathelicidin, referred to alternatively as FALL-39, hCAP18, LL-37, or CAMP, in its active processed form is a 37-amino acid amphiphilic α-helical cationic peptide. See Zanetti et al., *FEBS Lett.* 374: 1-5(1995). Expression of LL-37 has been detected in human neutrophils, testicular cells, respiratory epithelia, and in keratinocytes at sites of inflammation.

The amphipathic cationic peptides of the α-helical class typically demonstrate minimal bactericidal concentrations in the μg/mL range, which is comparable to other antimicrobial agents. Amphipathic cationic peptides are able to kill a broad range of gram-negative and gram-positive bacterial pathogens, including those that are highly resistant to multiple antibiotics. See Hancock, *Drugs* 57: 469-73 (1999). These peptides kill bacteria first by binding the negatively charged bacterial surface and then inserting into the bacterial membrane, disrupting its structural integrity. The hallmark of amphipathic cationic α-helical antimicrobial peptides is their capacity to fold into an amphipathic secondary structure that presents a hydrophilic face with a net positive charge of at least +2. A number of different amino acid sequence combinations allow a peptide to achieve this characteristic structure. Consequently, hundreds of host-derived amphipathic cationic α-helical peptides have been described to date all showing limited sequence homology at the level of primary sequence comparison. See Hwang et al., *Biochem. Cell Biol.* 76: 235-46 (1998). The screening assays described above for RIPs also may be used to screen antimicrobial peptides for activity, especially in the form of a composition comprising both a RIP and an antimicrobial peptide.

The terms "protein," "polypeptide," or "peptide," as used herein with reference to both RIP and antimicrobial peptides, include modified sequences (e.g., glycosylated, PEG-ylated, containing conservative amino acid substitutions, containing protective groups, including 5-oxoprolyl, amidation, D-amino acids, etc.). Amino acid substitutions include conservative substitutions, which are typically within the following groups: glycine, alanine; valine, isoleucine, leucine; aspartic acid, glutamic acid; asparagine, glutamine; serine, threonine; lysine, arginine; and phenylalanine, tyrosine. The skilled artisan appreciates that antimicrobial peptides do not include conventional antibiotics.

Proteins, polypeptides and peptides of the invention may be naturally occurring or produced recombinantly or by chemical synthesis according to methods well known in the art. The artisan skilled in this art is aware of various methods of recombinantly producing antimicrobial peptides in a bacterial host, despite the toxicity of the native peptides to bacteria. U.S. Pat. Nos. 5,589,364 and 5,789,377, incorporated herein by reference in its entirety, provide two examples of disclosures of suitable methods of recombinant production of amphiphilic peptides with biologically and therapeutically significant activities. For example, *E. coli* protease-deficient K-12 cells are transformed with a vector that expresses a cleavable fusion protein comprising at least part of a carbohydrate binding protein and an amphiphilic antimicrobial peptide. The fusion protein is expressed in the cell, the carbohydrate binding portion facilitates purification of the expressed fusion protein, and the fusion protein is then cleaved to obtain the amphiphilic peptide substantially free of carbohydrate binding protein residues. The biologically active amphiphilic peptide so produced may be further treated chemically or enzymatically to obtain a chemically distinct amphiphilic antimicrobial peptide with desired biological and therapeutic properties. In one embodiment, a DNA encoding a RIP may be co-expressed with a DNA encoding an antimicrobial peptide, so that recombinant expression produces both a RIP and an antimicrobial peptide. For example, the encoding DNAs may be contained on the same genetic construct under the operable control on the same promoter. In another embodiment, the reading frames of the encoding DNAs are fused in-frame, so that the construct expresses a fusion protein containing both RIP and antimicrobial peptide sequences. See Balaban et al., *Antimicrob. Agents Chemother.* 48: 2544-50 (2004).

Proteins, polypeptides and peptides of the invention can be purified or isolated. "Purified" refers to a compound that is substantially free, e.g., about 60% free, about 75% free, or about 90% free, from components that normally accompany the compound as found in its native state. An "isolated" compound is in an environment different from that in which the compound naturally occurs.

Pharmaceutical Compositions and Treatment Modalities

The term "treatment" or "treating" means any therapeutic intervention in an individual animal, e.g. a mammal, preferably a human. Treatment includes (i) "prevention," causing the clinical symptoms not to develop, e.g., preventing infection from occurring and/or developing to a harmful state; (ii) "inhibition," arresting the development of clinical symptoms, e.g., stopping an ongoing infection so that the infection is eliminated completely or to the degree that it is no longer harmful; and (iii) "relief," causing the regression of clinical symptoms, e.g., causing a relief of fever and/or inflammation caused by an infection. Treatment may comprise the prevention, inhibition, or relief of biofilm formation. Administration to an individual "at risk" of having a bacterial infection means that the individual has not necessarily been diagnosed with a bacterial infection, but the individual's circumstances place the individual at higher than normal risk for infection of infection, e.g. the individual is a burn victim. Administration to an individual "suspected" of having a bacterial infection means the individual is showing some initial signs of infection, e.g. elevated fever, but a diagnosis has not yet been made or confirmed.

The term "effective amount" means a dosage sufficient to provide treatment. The quantities of active ingredients necessary for effective therapy will depend on many different factors, including means of administration, target site, physiological state of the patient, and other medicaments administered; therefore, treatment dosages should be titrated to optimize safety and efficacy. Typically, dosages used in vitro may provide useful guidance in the amounts useful for in vivo administration of the active ingredients. Animal testing of effective doses for treatment of particular disorders will provide further predictive indication of human dosage. The concentration of the active ingredients in the pharmaceutical formulations typically vary from less than about 0.1%, usually at or at least about 2% to as much as 20% to 50% or more by weight, and will be selected primarily by fluid volumes, viscosities, etc., in accordance with the particular mode of administration selected. Various appropriate considerations are described, for example, in Goodman and Gilman, "The Pharmacological Basis of Therapeutics," Hardman et al., eds., 10$^{th}$ ed., McGraw-Hill, (2001) and "Remington: The Science and Practice of Pharmacy," University of the Sciences in Philadelphia, 21$^{st}$ ed., Mack Publishing Co., Easton Pa. (2005), both of which are herein incorporated by reference in their entirety. Methods for administration are discussed therein, including administration by oral, intravenous, intraperitoneal, intramuscular, transdermal, nasal, and iontophoretic routes, and the like.

The compositions of the invention may be administered in a variety of unit dosage forms depending on the method of administration. For example, unit dosage forms suitable for oral administration include solid dosage forms such as powder, tablets, pills, and capsules, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like.

Examples of inactive ingredients that may be added to the composition of the invention include agents that provide desirable color, taste, stability, buffering capacity, dispersion or other features, such as red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The compositions of the invention may also be administered via liposomes, including emulsions, foams, micelles, insoluble monolayers, liquid crystals, phospholipid dispersions, lamellar layers and the like. In these preparations the composition of the invention to be delivered may be incorporated as part of the liposome, alone or in conjunction with a targeting molecule, such as antibody, or with other therapeutic or immunogenic compositions. Thus, liposomes either filled or decorated with a desired composition of the invention of the invention can delivered systemically or can be directed to a tissue of interest.

Liposomes for use in the invention are formed from standard vesicle-forming lipids, which generally include neutral and negatively charged phospholipids and a sterol, such as cholesterol. The selection of lipids is generally guided by the desired liposome size, acid lability and stability in the blood stream. A variety of methods are available for preparing liposomes as described in Szoka et al., *Ann. Rev. Biophys. Bioeng.* 9: 467 (1980), U.S. Pat. Nos. 4,235,871, 4,501,728, 4,837,028, and 5,019,369, which are incorporated herein by reference. A liposome suspension containing a composition of the invention may be administered intravenously, locally, topically, etc. in a dose which varies according to the manner of administration, the composition of the invention being delivered, and the stage of the disease being treated, among other things.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, and more preferably at a concentration of 25%-75%. The constructs of the invention can additionally be delivered in a depot-type system, an encapsulated form, or an implant by techniques well-known in the art. Similarly, the constructs can be delivered via a pump, e.g. an osmotic pump, to a tissue of interest.

For aerosol administration, the compositions of the invention are preferably supplied in finely divided form along with a surfactant and propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

For the purpose of the invention, "administration of a composition" includes the administration of separate formulations of the RNAIII-inhibiting peptide and the antimicrobial peptide(s) and/or antibiotic(s) to the same individual at or around the same point in time, such that therapeutic concentrations of each active ingredient are achieved at the same time in the individual. The term also includes administering an antibiotic(s) to the individual in the same formulation that comprises the RIP and antimicrobial peptide, or administering the antibiotic(s) as a separate formulation at or around the same time as the RIP and antimicrobial peptide are administered. For example, the present method comprises oral co-administration of separate pills containing RIP, an antimicrobial peptide and an antibiotic. Useful antibiotics include aminoglycosides (e.g., gentamycin), beta-lactams (e.g., penicillin), cephalosporin or vancomycin. Administration of the RIP and antimicrobial peptide may occur within about 48 hours and preferably within about 2-8 hours, and most preferably, substantially concurrently with administration of the antibiotic.

The compounds having the desired pharmacological activity may be administered in a physiologically acceptable carrier to a host for treatment, prevention, inhibition or relief of pathogenic bacterial infection. The therapeutic agents may be administered in a variety of ways, such as orally, topically, parenterally, intraperitoneally, intravascularly, intrapulmonary (i.e., inhalation), etc. Depending upon the manner of introduction, the compounds may be formulated in a variety of ways.

The concentration of therapeutically active compound in the formulation may vary from about 0.1-100 wt. %. The dosage regimen may be adjusted to provide the optimum therapeutic response. For example, several divided doses may be administered daily or the dose may be proportionally reduced as indicated by the therapeutic situation. Human dosage levels for treating infections are known and generally include a daily dose from about 0.1 to 500 mg/kg of body weight per day, preferably about 6 to 200 mg/kg, and most preferably about 12 to 100 mg/kg. The amount of formulation administered will, of course, be dependent on the subject and the severity of the affliction, the manner and schedule of administration and the judgment of the prescribing physician. Generally, serum concentrations should be maintained at levels sufficient to treat infection in less than 10 days, although an advantage offered by the present invention is the ability to extend treatment for longer than 10 days at relatively low levels of the composition because of the decreased likelihood that bacteria will develop resistance to the present composition over treatment.

The pharmaceutical compositions can be prepared in various forms, such as granules, tablets, pills, suppositories, capsules, suspensions, salves, lotions and the like. Pharmaceutical grade organic or inorganic carriers or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The compositions may include other pharmaceutical excipients, carriers, etc. Suitable excipients are, for example, water, saline, dextrose, glycerol, ethanol or the like. Methods of preparing pharmaceutical compositions are well known to those skilled in the art. See, for example, "Remington: The Science and Practice of Pharmacy," University of the Sciences in Philadelphia, 21$^{st}$ ed., Mack Publishing Co., Easton Pa. (2005).

The present composition is useful in reducing the overall pathology or delaying the onset of disease symptoms in various diseases caused by bacterial infection in addition to bacterial sepsis, including bacterial-induced systemic inflammatory syndrome (SIRS), cellulitis, keratitis, osteomyelitis, septic arthritis, mastitis, skin infections, pneumonia, endocarditis, meningitis, post-operative wound infections, device-associated infections and toxic shock syndrome.

Treatment of Biofilm-Related Infections

Bacteria that attach to surfaces aggregate in a hydrated polymeric matrix of their own synthesis to form biofilms. Formation of these sessile communities and their inherent resistance to antimicrobial agents are at the root of many persistent and chronic bacterial infections. See Costerton et al., Science 284: 1318-22 (1999). Biofilms develop preferentially on inert surfaces, or on dead tissue, and occur commonly on medical devices and fragments of dead tissue such as sequestra of dead bone; they can also form on living tissues, as in the case of endocarditis. Biofilms grow slowly, in one or more locations, and biofilm infections are often slow to produce overt symptoms. Sessile bacterial cells release antigens and stimulate the production of antibodies, but the antibodies are not effective in killing bacteria within biofilms and may cause immune complex damage to surrounding tissues. Even in individuals with excellent cellular and humoral immune reactions, biofilm infections are rarely resolved by the host defense mechanisms. Antibiotic therapy typically reverses the symptoms caused by planktonic cells released from the biofilm, but fails to kill the biofilm. For this reason biofilm infections typically show recurring symptoms after cycles of antibiotic therapy, until the sessile population is surgically removed from the body. It is therefore preferable to prevent biofilm formation rather than to try to eradicate biofilms once they have formed.

The compositions and methods of the present invention are useful in the treatment of bacterial infection associated with biofilms, or in reducing the risk of a disease associated with biofilms, particularly biofilms caused by bacteria whose pathogenicity is related to a lipidic and polyanionic components of the bacterial cell envelope. For example, a composition comprising a RIP and an antibiotic, such as an aminoglycoside, a beta-lactam, cephalosporin or vancomycin, may be used to treat or reduce the risk of biofilms. In another embodiment, the RIP is combined with an antimicrobial peptide in addition to, or instead of, a conventional antibiotic to treat or reduce the risk of an infection associated with a biofilm.

The present composition may be used to coat devices that are inserted into an individual, e.g., a surgical device, catheter, prosthetic or other implant, to reduce the risk that the implanted device will develop a biofilm. Alternatively, the composition may be implanted to provide a high, localized concentration of the composition in the treatment of a localized infection. In this embodiment, the composition may be provided in a depot and formulated for sustained release. Table 2 below provides a partial list of nosocomial infections, for which the present composition and method are expected to be useful.

TABLE 2

| Medical device or device-associated disease | Bacterial species typically responsible for associated biofilms |
|---|---|
| Sutures | S. aureus and S. epidermidis |
| Exit sites | S. aureus and S. epidermidis |
| Arteriovenous shunts | S. aureus and S. epidermidis |
| Schleral buckles | Gram-positive cocci |
| Contact lens | P. aeruginosa and Gram-positive cocci |
| Urinary catheter cystitis | E. coli and other Gram-negative rods |
| Peritoneal dialysis (CAPD) peritonitis | Staphylococcus; various bacteria and fungi |
| Endotracheal tubes | A variety of bacteria and fungi |
| Hickman catheters | S. epidermidis and C. albicans |
| ICU pneumonia | Gram-negative rods |
| Central venous catheters | S. epidermidis and others |
| Mechanical heart valves | S. aureus and S. epidermidis |
| Vascular grafts | Gram-positive cocci |
| Orthopedic devices | S. aureus and S. epidermidis |
| Penile prostheses | S. aureus and S. epidermidis |

1. EXAMPLE

A composition comprising RIP and BMAP-28 was administered to RAW 264.7 cells in vitro. The composition was found to inhibit the LTA-induced release of TNF-α and the production of NO, a powerful vasodilator that contributes to the circulatory collapse in various animal models of septic shock. In a separate study, a composition comprising RIP and BAMP-28 was shown to be effective in a mouse sepsis model.

1.1 Materials and Methods:

Organisms: The commercially available quality control strain of S. aureus ATCC 25923 was used.

Reagents: LTA from S. aureus (Sigma-Aldrich, Milan, Italy) was resuspended in endotoxin-free water, aliquoted and stored at −20° C. for short periods. LPS contamination of the LTA preparation was less than 2 ng/mL, as determined by the Limulus assay from BioWhittaker (Walkersville, Md., USA).

PAL-PEG-PS resin, coupling reagents for peptide synthesis and Fmoc-amino acids were purchased from Applied Biosystems (Foster City, USA). Peptide synthesis-grade N,N-dimethylformamide, N-methyl-2-pyrrolidone, dichloromethane and HPLC-grade acetonitrile were from Biosolve (Valkenswaard, The Netherlands). Trifluoroacetic acid, N-methylmorpholine and trifluoroethanol (TFE) were from Acros Chimica (Beerse, Belgium).

Agents: The amide form of native RIP (YSPWTNF-NH$_2$) was synthesized by Neosystem (Strasbourg, France) and purified by HPLC to 99%. RIP powder was dissolved in distilled H$_2$O at 20 times the required maximal concentration.

BMAP-28 (GGLRSLGRKILRAWKKYGPIIVPIIRI-NH$_2$; SEQ ID NO: 1) was chemically synthesized as a C-terminally amidated peptide on a Milligen 9050 automated synthesizer (Applied Biosystems, Foster City, USA) using Fmoc chemistry. See Skerlavaj (1996). Molecular mass was determined by electrospray mass spectrometry (ES-MS), using an API I instrument (PE SCIEX, Toronto, Canada). The purified peptide was dissolved in endotoxin-free water, aliquoted, and stored at −20° C. Peptide concentration was determined by measuring the absorbance of BMAP-28 at 280 nm and considering a molar extinction coefficient of 5559 for Trp and of 1280 for Tyr.

Depending on the assay, serial dilutions of the peptide were prepared (i) in the cell culture medium for the in vitro assays on RAW 264.7 cells, (ii) in 0.01% acetic acid containing 0.2% bovine serum albumin in polypropylene tubes for in vitro susceptibility tests, and (iii) in physiological saline for in vivo experiments. Imipenem (Merck, Sharp & Dohme, Milan, Italy) and vancomycin (Sigma-Aldrich) powders were diluted in accordance with manufacturers' recommendations. All solutions were made fresh on the day of assay. The concentration range assayed for each compound was 0.25-256 mg/L.

Cytokine production by RAW 264.7 cells: The murine macrophage cell line RAW264.7 was obtained from American Type Culture Collection (ATCC) and maintained in RPMI supplemented with 10% fetal calf serum (FCS), 2 mM L-glutamine, 100 units/mL penicillin and 100 µg/mL streptomycin in a humidified 37° C. incubator. RAW264.7 cells were plated in 24-well dishes at $10^6$ cells/well in the above medium and incubated at 37° C. in 5% $CO_2$ overnight. RPMI was aspirated from cells grown overnight and replaced with fresh medium. Cells were incubated with 5 µg/mL LTA from *Staphylococcus aureus* at 37° C. in 5% $CO_2$ in the absence or the presence of each peptide at the following concentrations: 2 µM BMAP-28; 4 µM BMAP-28; 20 µM RIP; 20 µM RIP in combination with 2 µM BMAP-28. Peptides were added simultaneously with LTA. After 24 hours incubation, the supernatants were removed and tested for TNF-α production by enzyme linked immunosorbent assay (ELISA; Euroclone Life Sciences, Milan, Italy) according to the manufacturer's specification. All samples were run in duplicate. The detection limit for TNF-α was <0.025 ng/mL. To demonstrate the specificity of action of RIP, a supplementary experiment was performed with 20 µg/mL of an inactive RIP peptide analogue (YKPETNF-NH$_2$, Neosystem, Strasbourg, France).

Nitric oxide (NO) detection: RAW264.7 cells were cultured as described above. The amount of LTA-stimulated production of NO in the supernatant over 24 hours was estimated from the accumulation of the stable NO metabolite nitrite with Griess reagent (Molecular Probes, Eugene, Oreg.) according to the manufacturer's instructions.

Susceptibility testing: Susceptibilities to the antibiotics were determined by using the microbroth dilution method, according to the procedures outlined by the National Committee for Clinical Laboratory Standards, "Methods for dilution antimicrobial susceptibility tests for bacteria that grow aerobically": Approved standard M7-A6, Villanova, Pa. (2003). The MIC was taken as the lowest antibiotic concentration at which observable growth was inhibited. Experiments were performed in triplicate.

Animals: BALB/c male mice weighing 23 to 30 g were used for all the experiments. All animals were housed in individual cages under constant temperature (22° C.) and humidity with a 12 hour light/dark cycle and had access to food and water ad libitum throughout the study. The study was approved by the animal research ethics committee of the I.N.R.C.A.-I.R.R.C.S., Polytechnic University of Marche, Ancona, Italy.

Preparation of the inoculum: *S. aureus* ATCC 25923 were grown overnight at 37° C. in brain-heart infusion broth. When bacteria were in the log phase of growth the suspension was centrifuged at 1000× g for 15 min, the supernatant was discarded, and the bacteria were resuspended in sterile saline to achieve a concentration of approximately $1 \times 10^7$ CFU/mL.

Heat-killed *S. aureus* were prepared by boiling for 10 min and sonicating a bacterial suspension for 1 min in phosphate buffered saline containing approximately $2.5 \times 10^9$ cells/mL. The efficacy of the heat treatment was confirmed by culturing the bacteria overnight to ensure that there was no growth.

Implantation of inoculum: All animals were anesthetized by an intramuscular injection of ketamine (30 mg/kg of body weight). Mice were injected intravenously (i.v.) via the tail vein with 0.2 mL of the above mentioned bacterial suspensions: (i) $2.0 \times 10^6$ CFU of *S. aureus* ATCC 25923 (model 1), or (ii) $5.0 \times 10^8$ heat-killed cells (model 2) on day 0 and monitored for 72 hours.

Antibiotic therapy. Immediately (models 1a and 2a) or six hours (models 1b and 2b) after bacterial challenge, the mice were randomized to receive intravenously isotonic sodium chloride solution (control group), 10 mg/kg RIP alone or combined with 2 mg/kg BMAP-28, 7 mg/kg imipenem, and 7 mg/kg vancomycin. Each group included 20 mice. The animals were returned to individual cages and monitored for the subsequent 72 hours. The endpoints of the study were lethality rates (model 1), quantitative blood cultures (bacteremia, model 1), and TNF-α or IL-6 plasma levels (model 2). Toxicity was evaluated on the basis of the presence of drug related adverse effects (local signs of inflammation, weight loss, vomiting, diarrhea and fever) in a supplementary RIP and BMAP-28-treated groups without challenge.

Evaluation of treatment: Blood samples for culture were obtained from the tail vein by aseptic percutaneous puncture 24 h after bacterial challenge. The animals that died before this time were not tested. To perform quantitative bacterial cultures, blood samples were serially diluted, a 0.1 mL volume of each dilution was spread on blood agar plates and cultured at 35° C. for 48 h, and colony forming units (CFU) were counted. The limit of detection was <10 CFU/mL.

Plasma TNF-α and IL-6 levels. To determine TNF-α and IL-6 in plasma (model 2), blood samples were collected from the tail vein after 0, 6, 12, 24 and 48 h post-injection. TNF-α levels were measured with a solid phase sandwich enzyme-linked immunosorbent assay (ELISA). The intensity of the color was measured in a MR 700 Microplate Reader (Dynatech Laboratories, Guernsey, United Kingdom) by reading the absorbance at 450 nm. The results for the samples were compared with the standard curve to determine the amount of TNF-α present. All samples were performed in duplicate. The lower limit of sensitivity for TNF-α by this assay was 0.05 ng/mL. The plasma concentrations of IL-6 were also determined by ELISA, as described above. Quantification was performed on the basis of a standard curve. The detection limit was 12 pg/mL. The assays were performed in duplicate.

Statistical analysis: Lethality rates between groups were compared by use of Fisher's exact test. Data from quantitative blood cultures were presented as means±standard deviations (SDs) of the mean; statistical comparisons between groups were made by analysis of variance. Post hoc comparisons were performed by Bonferroni's test. Plasma IL-6 and TNF-α mean values were compared between groups by analysis of variance. Significance was accepted when the p value was <0.05.

1.2 Results:

Cytokine and NO production: To determine the effect of RIP and BMAP-28 on cellular responses mediated by LTA, the ability of these peptides, alone or in combination, to inhibit the LTA-induced production of TNF-α and NO by RAW264.7 cells was analyzed.

TNF-α levels ranged from 0.068 to 0.092 ng/mL in the supernatants of cells cultured in the absence of LTA and from 34.6 to 50.6 ng/mL in the presence of LTA. As shown in FIG. 1, RIP and BMAP-28, alone or in combination, decreased LTA-stimulated TNF-α production by RAW264.7 cells at every concentration tested. Data in FIG. 1 are presented as the mean±S.D. of at least three experiments.

Specifically, BMAP-28 decreased the LTA-induced release of TNF-α in a dose-dependent manner, with a 74.5±6% reduction at 2 µM peptide, and a nearly complete inhibition at 4 µM peptide, as shown in FIG. 1. Significantly, RIP alone at a 20 µM concentration reduced LTA-induced release of TNF-α by 45.6±10%. The combined presence of 20 µM RIP and 2 µM BMAP-28 produced an 85.4±3.1% inhibition (FIG. 1). At the concentrations used, neither peptide caused release of TNF-α and NO in the absence of LTA (not shown).

Figure 2:
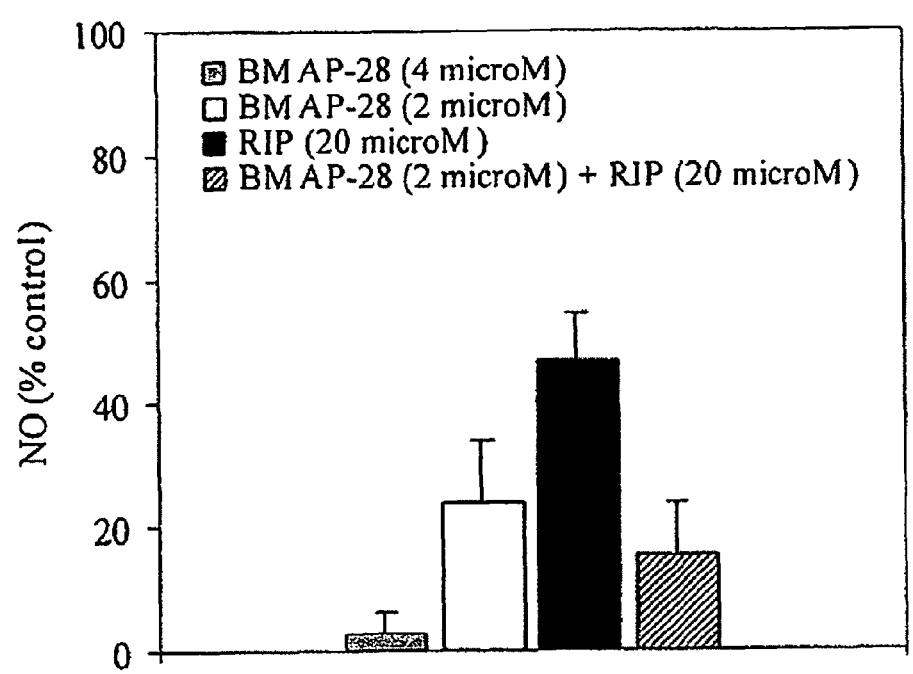
FIG. 2 depicts the effect of RIP and BMAP-28 on LTA-stimulated NO production as a percentage of control levels in cultured RAW264.7 cells. NO levels in the culture supernatant were measured 24 h after LTA stimulation in the presence of the reagents shown in the figure key.

Both peptides decreased the generation of LTA-stimulated NO when administered singly, with a reduction of 76±9.8% and 53.3±8.1% for 2 µM BMAP-28 and 20 µM RIP, respectively. The levels of NO were further decreased when RIP was combined with BMAP-28 (84.7±8.8% inhibition) (FIG. 2). Inhibitory effects of RIP were specific because the inactive RIP peptide analogue did not demonstrate decrease of TNF-α and NO (data not shown). NO levels detected in the supernatants of cells cultured in the absence or presence of LTA ranged from 5.98 to 9.17 µM and from 24.39 to 26.42 µM, respectively. Data in FIG. 2 are presented as the mean±S.D. of at least three experiments.

Significantly, RIP alone decreased LTA-stimulated TNF-α and NO production, which is the first time RIP has been shown to manifest these effects. While the invention is not limited by a proposed mechanism of action, this result suggests that, in addition to RIP's known inhibition of toxin production through inhibition of quorum sensing, RIP additionally may have the ability to inhibit bacterial induced sepsis through a separate mechanism. Further, the in vitro data is consistent with the notion that BMAP-28 directly binds LTA or its receptor on RAW264.7 cells.

Susceptibility testing: The Staphylococcal isolates showed susceptibility to BMAP-28, imipenem, and vancomycin that exhibited MICs of 2.00, 0.50, and 0.25 mg/L, respectively. Finally, RIP did not demonstrate any in vitro killing activities against the two strains (MICs>256 mg/L), as expected by its mechanism of action.

Murine sepsis models: To test whether RIP and BMAP-28 could have a potential therapeutic value in treating sepsis, a previously described mouse sepsis model was applied. As inducers of sepsis, live $S.\ aureus$ ATCC25923 or heat killed cells of the same strain were used. Lethality rate, plasma bacterial count, and plasma TNF-α or IL-6 were evaluated in two animal models. In model 1, animals were treated immediately or 6 h post challenge with high titers of $S.\ aureus$, and bacteremia and mortality were recorded. In model 2, cytokine levels were determined after injection with bacteria that were heat-killed and sonicated. Treatment with drugs 6 h after bacterial challenge mimicked the clinical situation, where an interval between the onset of sepsis and the initiation of therapy is present. The effect of RIP and BMAP-28 was compared to commonly used antibiotics.

Model 1a: (immediate treatment post challenge): As shown in Table 3A, when mice were challenged with $S.\ aureus$ ATCC 25923 and immediately treated with saline (control group $C_1$), the rate of lethality in was 100% within 72 hours. In contrast, immediate treatment with drugs demonstrated efficacy significantly higher than controls (P<0.05). Specifically, lethality rates of 30%, 20%, 30%, and 70% were observed for groups treated with imipenem, vancomycin, BMAP-28 and RIP, respectively. The combination of RIP and BMAP-28 showed a significantly lower lethality rate of 5%; about two-fold lower lethality rates also were observed when RIP was combined with imipenem or vancomycin, compared to the lethality rates when the antibiotics were administered without RIP.

In the same model, quantitative blood culture in the control group showed $4.3±1.1×10^6$ CFU/mL (Table 3A). BMAP-28 showed antibacterial activity with values of $3.7±0.9×10^3$ CFU/mL, while vancomycin alone showed lower counts ($7.8±1.8×10^1$ CFU/mL). When vancomycin was combined with RIP, the synergistic interaction of the two drugs produced the lowest bacterial counts ($2.8±0.6×10^1$ CFU/mL). Finally, all combination treated groups had significant lower bacterial counts when compared to the imipenem- and the BMAP-treated groups (P<0.05).

Model 1b (treatment 6 h post challenge): As shown in Table 3B, the effect of administration of drugs 360 min after bacterial challenge on lethality rates and bacterial counts was comparable, although slightly lower, to that observed in the immediately treated groups. Again, the synergistic effect on CFU/mL between RIP and imipenem or vancomycin was roughly two-fold, compared to the effect of the antibiotics alone.

TABLE 3A

| Treatment[a] | Lethality[b] (dead/total %) | Qualitative Blood Culture (positive/total) | Quantitative Blood Culture (CFU/ml)[c] |
|---|---|---|---|
| No treatment (Control Group $C_1$) | 20/20 (100) | 20/20 | $9.5 ± 1.7 × 10^5$ |
| RIP 10 mg/Kg | $14/20^d$ (70) | $14/20^d$ | $4.0 ± 0.8 × 10^{4d}$ |
| BMAP-28 2 mg/Kg | $6/20^{de}$ (30) | $6/20^{df}$ | $3.7 ± 0.9 × 10^{3de}$ |
| VAN 7 mg/Kg | $4/20^{de}$ (20) | $5/20^{df}$ | $7.8 ± 1.8 × 10^{1deg}$ |
| IMP 7 mg/Kg | $6/20^{de}$ (30) | $7/20^{df}$ | $5.8 ± 1.4 × 10^{2de}$ |
| RIP 10 mg/Kg BMAP-28 2 mg/Kg | $1/20^{deh}$ (5) | $2/20^{df}$ | $3.7 ± 0.7 × 10^{2dg}$ |
| RIP 10 mg/Kg VAN 7 mg/Kg | $3/20^{de}$ (15) | $3/20^{df}$ | $2.8 ± 0.6 × 10^{1dg}$ |
| RIP 10 mg/Kg IMP 7 mg/Kg | $4/20^{de}$ (20) | $4/20^{df}$ | $2.8 ± 1.1 × 10^{2dg}$ |

[a]VAN, vancomycin; IMP, imipenem.
[b]Mortality was monitored for 72 h following the challenge.
[c]Mean ± S.D.
[d]P < 0.05 (Fisher's test) or P < 0.05 (Bonferroni's test) versus the control group $C_1$.
[e]P < 0.05 (Fisher's test) or P < 0.05 (Bonferroni's test) versus the RIP-treated group.
[f]P < 0.05 versus the RIP-treated group.
[g]P < 0.05 versus BMAP-28 treated group.
[h]P < 0.05 versus the VAN-, IMP-, RIP/IMP-treated groups.

TABLE 3B

| Treatment[a] | Lethality[b] (dead/total (%)) | Qualitative Blood Culture (positive/total) | Quantitative Blood Culture (CFU/ml)[c] |
|---|---|---|---|
| No treatment (Control Group $C_1$) | 20/20 (100) | 20/20 | $2.7 ± 0.3 × 10^6$ |
| RIP 10 mg/Kg | $15/20^d$ (70) | $15/20^d$ | $5.6 ± 1.2 × 10^{4d}$ |
| BMAP-28 2 mg/Kg | $6/20^{de}$ (30) | $6/20^{df}$ | $5.7 ± 1.8 × 10^{3de}$ |
| VAN 7 mg/Kg | $4/20^{de}$ (20) | $5/20^{df}$ | $9.0 ± 2.8 × 10^{1deg}$ |
| IMP 7 mg/Kg | $7/20^{de}$ (35) | $7/20^{df}$ | $7.1 ± 1.7 × 10^{2de}$ |
| RIP 10 mg/Kg BMAP-28 2 mg/Kg | $1/20^{deh}$ (5) | $3/20^{df}$ | $3.9 ± 0.9 × 10^{2dg}$ |
| RIP 10 mg/Kg VAN 7 mg/Kg | $3/20^{de}$ (15) | $3/20^{df}$ | $3.6 ± 1.4 × 10^{1dg}$ |
| RIP 10 mg/Kg IMP 7 mg/Kg | $5/20^{de}$ (20) | $5/20^{df}$ | $3.9 ± 1.2 × 10^{2dg}$ |

[a]VAN, vancomycin; IMP, imipenem.
[b]Mortality was monitored for 72 h following the challenge.
[c]Mean ± S.D.
[d]P < 0.05 (Fisher's test) or P < 0.05 (Bonferroni's test) versus the control group $C_1$.
[e]P < 0.05 (Fisher's test) or P < 0.05 (Bonferroni's test) versus the RIP-treated group.
[f]P < 0.05 versus the RIP-treated group.
[g]P < 0.05 versus BMAP-28 treated group.
[h]P < 0.05 versus the VAN-, IMP-, RIP/IMP-treated groups.

Figure 3A:
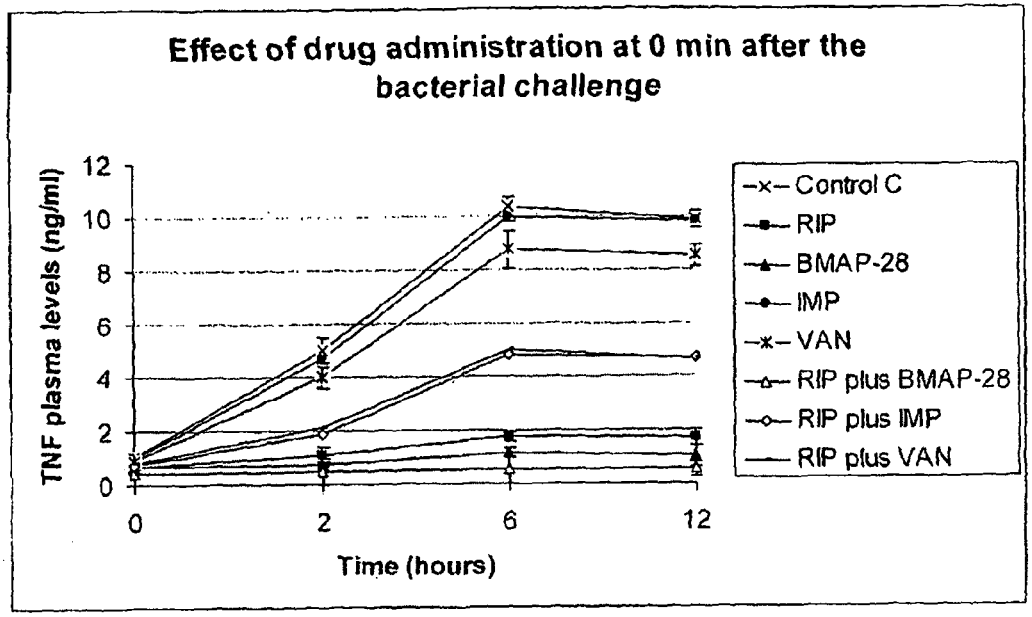
FIG. 3A shows the effect of administration of various drugs at 0 min after bacterial challenge on TNF-α plasma levels (ng/mL) as a function of time (hours) in a mouse model. RNAIII-inhibiting peptide is abbreviated "RIP"; BMAP-28 is a bovine antimicrobial peptide; imipenem is abbreviated "IMP", and vancomycin is abbreviated "VAN".
Figure 4A:
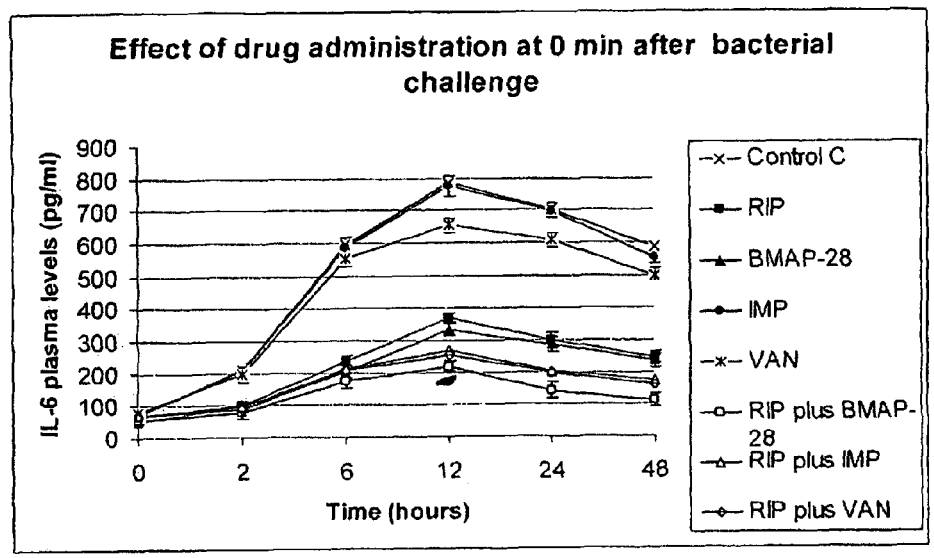
FIG. 4A shows the effect of administration of various drugs at 0 min after bacterial challenge on IL-6 plasma levels (pg/mL) as a function of time (hours) in a mouse model.

Model 2a (TNF-α and IL-6 production in vivo): Plasma peak levels of TNF-α and IL-6 were respectively observed 6 h and 12 h after intravenous administration of 0.2 mL of heat-killed cells. RIP and BMAP-28 treatments (alone or combined) resulted in marked decrease (P<0.05) of TNF-α and IL-6 plasma levels compared with those of control group, imipenem or vancomycin. No substantial differences in the plasma levels of cytokines were observed among the groups treated or untreated with conventional antibiotics (FIGS. 3A and 4A). Finally, the strongest reduction in TNF-α and IL-6 plasma levels was observed in the group treated with the combination of RIP and BMAP-28, although the combination of RIP and the antibiotics imipenem or vancomycin also reduced TNF-α and IL-6 plasma levels.

Figure 3B:
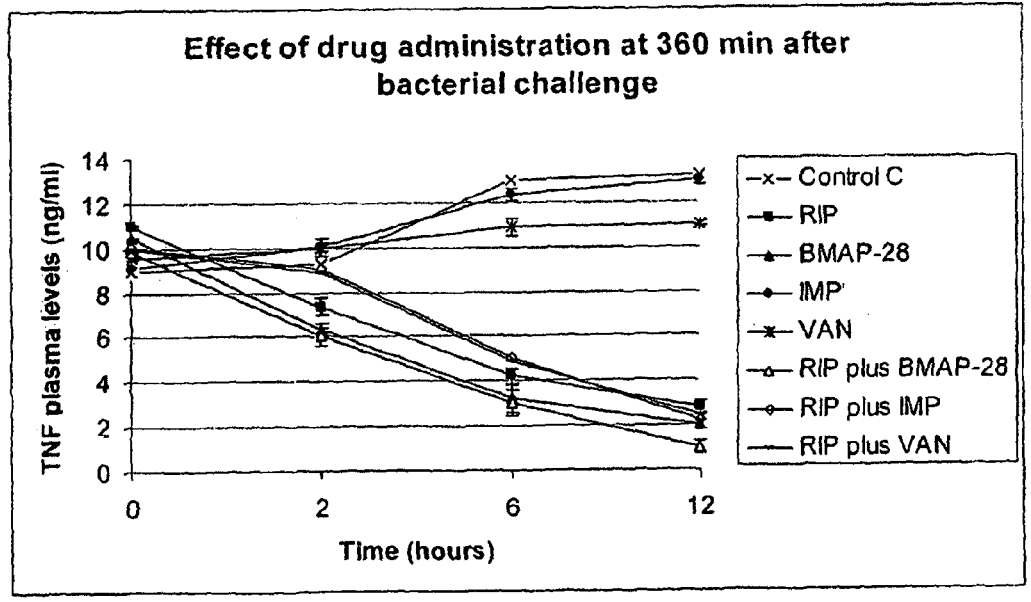
FIG. 3B shows the effect of administration of various drugs 360 min (6 h) after bacterial challenge on TNF-α plasma levels (ng/mL) as a function of time (hours) in a mouse model.
Figure 4B:
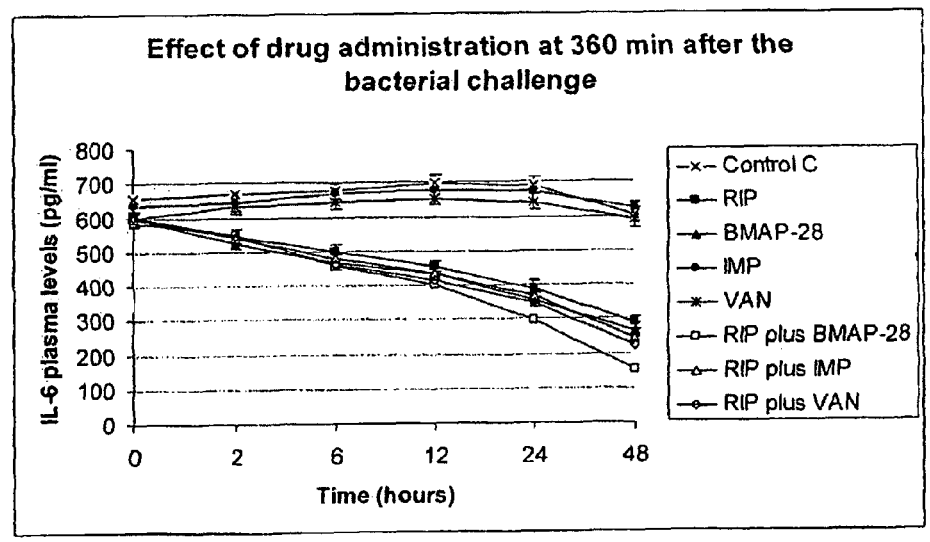
FIG. 4B shows the effect of administration of various drugs 360 min (6 h) after bacterial challenge on IL-6 plasma levels (pg/mL) as a function of time (hours) in a mouse model.

Model 2b (TNF-α and IL-6 production in vivo): The administration of drugs at 360 min after heat-killed bacterial challenge had a different impact on plasma cytokines levels. In fact, a constant increase in plasma TNF-α and IL-6 concentrations was observed in controls, imipenem and vancomycin treated mice, while a constant decrease was induced by the administration of RIP and BMAP-28 360 min after bacterial challenge and by their combination (FIGS. 3B and 4B). Overall, RIP and BMAP-28 and their combination produced a significant reduction in plasma cytokines levels compared to the control and to the imipenem- and vancomycin-treated groups. Interestingly, significant differences were also observed between imipenem and vancomycin. Similarly to model 2a, the combinations between RIP and BMAP-28 produced the strongest reduction in TNF-α and IL-6 plasma levels.

Finally, none of the animals had clinical evidence of drug-related adverse effects and no changes in physiological parameters were observed in the supplementary RIP- and BMAP-28-treated groups without previous infection.

The best results on mortality rate and bacteremia were obtained when RIP was combined with BMAP-28, suggesting that their mode of action is complementary. A combination of RIP and BMAP-28 was also most effective in decreasing the levels of cytokines, confirming the capacity of the two drugs to inhibit toxin production and neutralize cell wall components that are the inducers of cytokine activation.

All publications and patents mentioned herein are incorporated herein by reference to disclose and describe the specific methods and/or materials in connection with which the publications and patents are cited. The publications and patents discussed herein are provided solely for their disclosure prior to the filing date of the present application. Nothing herein is to be construed as an admission that the present invention is not entitled to antedate such publication or patent by virtue of prior invention. Further, the dates of publication or issuance provided may be different from the actual dates which may need to be independently confirmed.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method of treating or reducing the risk of bacterial infection in a mammalian individual, comprising administering to said individual a composition comprising an amount of an isolated RNAIII-inhibiting peptide (RIP) and an antimicrobial peptide capable of binding and neutralizing a lipidic and polyanionic component of a bacterial cell envelope, where the RIP and antimicrobial peptide are present in an amount effective to treat or reduce the risk of a bacterial infection in said individual, where the bacterial infection is caused by *Staphylococcus* spp *Bacillus* spp., *B. subtilus*, *B. cereus*, *B. anthracis*, *Listeria* spp., *L. innocua*, *L. monocytogenes*, *Streptococcus pyogenes*, *Lactococcus lactis*, *Enterococcus faecalis*, *Escherichia coli*, or *Clostridium acetobtylicum*.

2. The method of claim 1, where the treating or reducing the risk of bacterial infection comprises preventing clinical symptoms from developing, inhibiting the development of clinical symptoms, or relieving clinical symptoms.

3. The method of claim 1, where the bacterial infection is caused by an antibiotic resistant bacteria.

4. The method of claim 1, where the bacterial infection is bacterial sepsis.

5. The method of claim 1, where the bacterial infection is localized to particular tissue, skin or region of the body.

6. The method of claim 1, where the infection is cellulitis, keratitis, osteomyelitis, septic arthritis or mastitis.

7. The method of claim 1, where the bacterial infection is associated with a biofilm.

8. The method of claim 1, where the bacterial infection is caused by *S. aureus*, or *S. epidermidis*.

9. The method of claim 1, where the administering is by a topical, oral, intravenous, intraperitoneal, intramuscular, transdermal, nasally, or iontophoretic route.

10. The method of claim 9, where the administering is by a depot-style system, an encapsulated form, an implant or a coating on a medical device.

11. The method of claim 1, further comprising administering an antibiotic to the individual.

12. The method of claim 1, where the individual is a human.

* * * * *

SEQUENCE LISTING

```
<160> NUMBER OF SEQ ID NOS: 12

<210> SEQ ID NO 1
<211> LENGTH: 27
<212> TYPE: PRT
<213> ORGANISM: Bovine

<400> SEQUENCE: 1

Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile
            20                  25

<210> SEQ ID NO 2
<211> LENGTH: 7
<212> TYPE: PRT
<213> ORGANISM: S. aureus
<220> FEATURE:
<221> NAME/KEY: MISC_FEATURE
<222> LOCATION: (2)..(2)
<223> OTHER INFORMATION: Xaa is Lys or Ser
<220> FEATURE:
<221> NAME/KEY: MISC_FEATURE
<222> LOCATION: (4)..(4)
<223> OTHER INFORMATION: Xaa is Cys, Trp, Ile or a modified amino acid

<400> SEQUENCE: 2

Tyr Xaa Pro Xaa Thr Asn Phe
1               5

<210> SEQ ID NO 3
<211> LENGTH: 7
<212> TYPE: PRT
<213> ORGANISM: S. aureus
<220> FEATURE:
```

```
<221> NAME/KEY: MISC_FEATURE
<222> LOCATION: (4)..(4)
<223> OTHER INFORMATION: Xaa is Cys, Trp, Ile or a modified amino acid

<400> SEQUENCE: 3

Tyr Ser Pro Xaa Thr Asn Phe
1               5

<210> SEQ ID NO 4
<211> LENGTH: 7
<212> TYPE: PRT
<213> ORGANISM: S. aureus
<220> FEATURE:
<221> NAME/KEY: MISC_FEATURE
<222> LOCATION: (4)..(4)
<223> OTHER INFORMATION: Xaa is Cys, Trp, Ile or a modified amino acid

<400> SEQUENCE: 4

Tyr Lys Pro Xaa Thr Asn Phe
1               5

<210> SEQ ID NO 5
<211> LENGTH: 10
<212> TYPE: PRT
<213> ORGANISM: S. aureus
<220> FEATURE:
<221> NAME/KEY: MISC_FEATURE
<222> LOCATION: (5)..(5)
<223> OTHER INFORMATION: Xaa is Lys or Ser
<220> FEATURE:
<221> NAME/KEY: MISC_FEATURE
<222> LOCATION: (7)..(7)
<223> OTHER INFORMATION: Xaa is Cys, Trp, Ile or a modified amino acid

<400> SEQUENCE: 5

Ile Lys Lys Tyr Xaa Pro Xaa Thr Asn Phe
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Pro Cys Thr Asn Phe
1               5

<210> SEQ ID NO 7
<211> LENGTH: 7
<212> TYPE: PRT
<213> ORGANISM: S. aureus

<400> SEQUENCE: 7

Tyr Lys Pro Ile Thr Asn Phe
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Tyr Lys Pro Trp Thr Asn Phe
1               5
```

```
<210> SEQ ID NO 9
<211> LENGTH: 8
<212> TYPE: PRT
<213> ORGANISM: S. aureus
<220> FEATURE:
<221> NAME/KEY: MISC_FEATURE
<222> LOCATION: (4)..(4)
<223> OTHER INFORMATION: Xaa is Lys or Ser
<220> FEATURE:
<221> NAME/KEY: MISC_FEATURE
<222> LOCATION: (6)..(6)
<223> OTHER INFORMATION: Xaa is Cys, Trp, Ile or a modified amino acid

<400> SEQUENCE: 9

Lys Lys Tyr Xaa Pro Xaa Thr Asn
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cys or Trp

<400> SEQUENCE: 10

Tyr Ser Pro Xaa Thr Asn Phe
1               5

<210> SEQ ID NO 11
<211> LENGTH: 6
<212> TYPE: PRT
<213> ORGANISM: S. aureus

<400> SEQUENCE: 11

Tyr Lys Pro Ile Thr Asn
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Tyr Ser Pro Trp Thr Asn Phe
1               5
```